United States Patent [19]

Cassaday et al.

[11] Patent Number: 4,602,995
[45] Date of Patent: Jul. 29, 1986

[54] LIQUID LEVEL ADJUSTING AND FILTERING DEVICE

[75] Inventors: Michael M. Cassaday, Valhalla, N.Y.; Rand Herron, Wilton, Conn.; Kenneth F. Uffenheimer, Yorktown Heights, N.Y.; John L. Smith, Bethlehem, Pa.

[73] Assignee: Technicon Instruments Corporation, Tarrytown, N.Y.

[21] Appl. No.: 735,847

[22] Filed: May 20, 1985

[51] Int. Cl.$^4$ ............................................. B01D 33/00
[52] U.S. Cl. .................... 210/120; 210/359; 210/406; 210/515; 210/516; 210/927
[58] Field of Search ............... 210/927, 359, 515, 516, 210/120, 406; 422/61

[56] References Cited

U.S. PATENT DOCUMENTS

3,481,477  12/1969  Farr ........................ 210/927
3,512,940   5/1970  Shapiro .................... 210/927
3,661,265   5/1972  Greenspan ................. 210/927

Primary Examiner—Frank Sever
Attorney, Agent, or Firm—Edward H. Gorman, Jr.; James R. Cartiglia; James J. Romano, Jr.

[57] ABSTRACT

New and improved, liquid level adjusting and filtering device is provided, and is operable upon insertion into a container to automatically adjust the level of a liquid as contained in the container to a predetermined, precisely repeatable location, and to filter the thusly level-adjusted liquid. The device is particularly adapted for use in conjunction with test tube-like devices, in the nature of those marketed under the Trademark "Vacutainer" by the Becton-Dickinson Company of East Rutherford, NJ, containing whole blood samples which have been separated as by centrifugation into respective blood cell, buffy and blood serum layers; and is operable in that context to present blood serum samples to automated sample analysis systems at the same predetermined and precisely repeatable location relative to the aspirating probe means of such systems.

17 Claims, 6 Drawing Figures

LIQUID LEVEL ADJUSTING AND FILTERING DEVICE

BACKGROUND OF THE INVENTION

1. Field of the Invention

This invention relates to a new and improved liquid level adjusting and filtering device which is automatically operable to adjust to a predetermined and precisely repeatable location the level of, and to filter, a liquid in a test tube or like container into which the device is inserted; and which is, in combination with said container, particulalrly adapted for use in automated sample liquid analysis systems to present each of a plurality of sample liquids in turn to the analysis system aspirating probe means at precisely the same level.

2. Description of the prior art

The most relevant prior art known to applicants is that embodied by the sample liquid filtering device as marketed under the Trademark "SERACLEAR" by applicants' assignee, Technicon Instruments Corporation, of Tarrytown, N.Y. Although, as illustrated and described in detail in this specification, this prior art filtering device does effectively function to filter a sample liquid in a test tube or like container into which the device is inserted for presentation to the aspirating probe means of an automated sample liquid analysis system, the same does not operate to automatically adjust the level of the thusly presented sample liquid to a predetermined and precisely repeatable location relative to those aspirating probe means.

Also relevant to this invention is the Serum Separator And Fibrin Filter as disclosed in U.S. Pat. No. 3,929,646 issued Dec. 30, 1975 to Stanford L. Adler and assigned to the assignee hereof. Although this separator does effectively function attendant sample liquid centrifugation with the separator inserted in the sample liquid container to separate and filter the blood serum constituent of a blood sample for presentation to the aspirating probe means of automated sample liquid analysis system, the same is again totally ineffective to automatically adjust the level of the thusly presented blood serum sample to a predetermined and precisley repeatable location relative to those aspirating probe means.

In addition, although automated sample liquid analysis systems are believed to now exist which include means to automatically adjust the level of the sample liquid containers to present the sample liquids as contained therein to the system aspirating probe means at the same level, these systems clearly do not anticipate the subject matter of this invention.

SUMMARY OF THE INVENTION

This invention provides a new and improved liquid level adjusting and filtering device for use with generally vertically oriented test tubes or like containers to automatically adjust the level of a liquid contained therein to a precisely determinable and repeatable location relative to the container, and to filter the thusly level-adjusted liquid. The device comprises a generally tubular member defining an internal space of lesser volume than the volume of the container, and including openings at both the upper and lower tubular member ends in communication with the internal space. The device operates through the insertion thereof into the container; and sealing and pumping means taking the form of a wiper are included in the tubular member at the lower member end, and are operable upon insertion of the tubular member into the container to contact the container wall and the liquid and positively pump the latter into the internal space through the lower opening in the tubular member. A filter is disposed in the lower tubular member opening, and is operable to filter the liquid as the same is pumped therethrough into the internal space. A cap member supports the thusly inserted tubular member in the container, and includes stop means operable to positively limit the extent to which the tubular member can be inserted into the container. The essential dimensions of the tubular member are predetermined in accordance with the essential dimensions of the container, and the amount of liquid normally expected to be contained therein in accordance with experience and careful testing, to insure that the insertion of the tubular member into the container to the maximum extent permitted by the stop means will result in the pumping by the wiper of sufficient liquid to fill and overflow the internal space, thus insuring a liquid level at a readily accessible, and precisely repeatable, location at the upper tubular member end opening. The cap member further includes overflow openings providing for the return of the excess, thusly pumped liquid to the container, and a vent opening for the venting of the ambient air displaced thereby back to atmosphere. For use with vertically layered liquids in the container, the tubular member is dimensioned in length to contact and pump liquid only from the uppermost of said liquid layers upon full insertion of the tubular member into the container.

The device is particularly adapted for use in conjunction with a Vacutainer containing a whole blood sample which has been separated as by centrifugation into respective blood cell, buffy, and blood serum layers; and is operable in conjunction therewith to present blood serum samples in turn to the aspirating probe of an automated blood sample analysis system at the same predetermined, and precisely repeated location relative to that probe. This renders the incorporation and use of blood sample level sensing devices unnecessary in the analysis system, and materially shortens the requisite vertical movement of the aspirating probe. To compensate for pre-analysis blood serum sample evaporation, the device may initially be inserted into the Vacutainer to slightly less than the full extent as permitted by the stop means, and means may be included in the analysis system to automatically complete such insertion just prior to presentation of the serum sample to the aspirating probe to replenish as needed the serum sample of interest at the upper tubular member end opening.

An appropriate chemical material for treatment of the blood serum may be included in the filter for treatment of the serum as the same is pumped therethrough by the wiper.

For use in sample analysis systems which utilize an immiscible isolation liquid or "oil" to minimize sample carryover, the device may be made hydrophilic.

OBJECTS OF THE INVENTION

It is, accordingly, an object of our invention to provide a new and improved device which is operable to automatically adjust the level of a liquid in a container into which the device is inserted to a predetermined, precisely repeatable location.

Another object of our invention is to provide a device as above which is operable to automatically filter said liquid upon the insertion thereof into said container.

Another object of our invention is the provision of a device as above which is of particularly simple and inexpensive configuration and manner of fabrication, and which is of one-piece construction and has no moving parts.

Another object of our invention is the provision of a device as above which is sufficiently inexpensive as to realistically disposable after only one use.

Another object of our invention is the provision of a device as above which is particularly adapted for use in conjunction with a container having vertically arranged liquid layers of different characteristics contained therein, and which is operable upon only the uppermost of said layers without effect on the other of said layers.

Another object of our invention is the provision of a device as above which is particularly adapted for use in an automated sample liquid analysis system for the presentation of each of a series of sample liquids in turn to the analysis system sample liquid aspirating probe means at precisely the same sample liquid level relative thereto.

Another object of our invention is the provision of a device as above which is operable to chemically treat said liquid concomitantly with the filtering thereof.

Another object of our invention is the provision of means operable in conjunction with said device in an automated sample liquid analysis system for compensating for the effects of pre-analysis liquid evaporation.

A further object of our invention is the provision of a device as above which is particularly adapted for use in conjunction with the blood serum layer of a blood sample which has been separated into respective blood cell, buffy and blood serum layers in a container for the automated analysis of the blood serum.

A further object of our invention is the provision of an automated sample analysis system incorporating the device of our invention.

DESCRIPTION OF THE DRAWINGS

The above and other objects and significant advantages of our invention are believed made clear by the following detailed description thereof taken in conjunction with the accompanying drawings wherein.

DETAILED DESCRIPTION OF THE INVENTION

Figure 1:
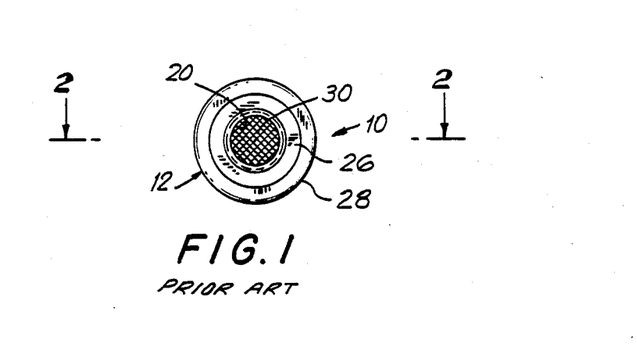
FIG. 1 is a bottom plan view of a liquid filtering device configured and operable in accordance with the principles of the prior art.
Figure 2:
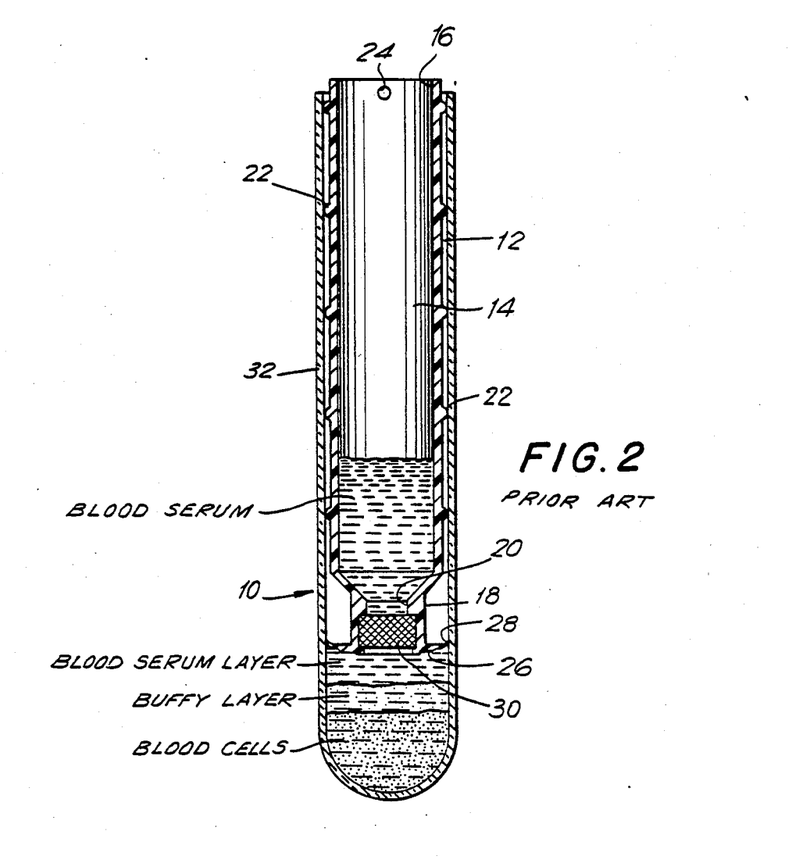
FIG. 2 is a cross sectional view taken essentially along line 2—2 in FIG. 1, and depicts the prior art device in operative relationship with a liquid container.

Referring initially to FIGS. 1 and 2, a liquid filtering device configured and operable in accordance with the principles of the prior art is indicated generally at 10; and may be understood to take the form of that marketed by our assignee, Technicon Instruments Corporation of Tarrytown, N.Y., under the Trademark "SERA-CLEAR."

The liquid filtering device 10 comprises a generally tubular body member 12 having an internal space 14. The body member 12 is open at the top end thereof as indicated at 16 in FIG. 2; and includes a necked-down portion 18 providing a stepped opening 20 of reduced diameter at the bottom end thereof. Spaced ribs 22 of uniform diameter are formed as shown on the body member 12 to extend radially outward thereof; and a vent hold 24 is formed as shown to extend through one wall only of the tubular body member 12 adjacent the top end thereof.

A generally torus-like wiper 26 is formed as shown integrally with the botton end of body member 12 to extend radially outward thereof in manner generally concentric with opening 20. Wiper 26 includes an outer edge or rim portion 28 which is of reduced thickness so as to be somewhat flexible; and the outer diameter of this edge or rim portion 28 is slightly greater than the outer diameter of the spaced body member ribs 22.

A generally cylindrical, mesh-like filter is indicated at 30 in FIGS. 1 and 2, and is disposed as shown in stepped opening 20 and retained therein in any suitable manner.

The body member 12 is preferably made from any readily available, inexpensive, suitably translucent and appropriately chemically inert material such as polyethylene; while filter 30 is preferably made from high density polyethylene of appropriate pore size.

In use to filter the upper layer of a liquid which has been separated into layers of different characteristics in a tubular container of inner diameter predetermined to form an interference fit with rim portion 28 of wiper 26—for example a blood sample which has been collected and centrifuged in a test tube as indicated at 32 in FIG. 2 to result in the separation of the blood sample into respective blood cell, buffy and blood serum layers as identified as such in FIG. 2—the liquid filtering device 10 of the prior art is manually inserted into the test tube 32 to come to rest with the wiper 26 remaining clearly above the serum-buffy layer interface as seen in FIG. 2. As this is accomplished, with the spaced ribs 22 acting as insertion guides to prevent the tubular body member 12 from "cocking" in the test tube 32, the wiper 26 will displace the blood serum layer downwardly and cause the blood serum to flow upwardly through filter 30 in opening 20 into the internal space 14 of the body member 12; thereby effectively filtering unwanted materials such as fibrin or clotted proteins or the like from the blood serum to result in a quantity of essentially "pure" blood serum contained within the internal space 14 as shown. Since it was determined that manual insertion of the liquid filtering device 10 into the test tube 32 as described is normally effected by the placement of the thumb over opening 16, vent hole 24 is provided to allow for the escape of ambient air as would otherwise be entrapped in the internal space 14 by the entry of the blood serum thereinto through filter 30.

FIG. 2 makes clear that the periphery of the wiper rim portion 28 may be slightly bent upwardly as shown attendant insertion as described of the device 10 into the test tube 32; and it will be understood by those skilled in this art that this insures an essentially liquid-tight interference fit between the wiper and the test tube wall, thus effectively preventing blood serum flow around the wiper and insuring amximum blood serum flow through filter 30 into internal space 14 commensurate with the amount of blood serum in the test tube 32 and the extent to which the device 10 is inserted thereinto. This is to say that the wiper 26 in essence acts as a positive displacement pump vis-a-vis the blood serum in test tube 32.

The liquid filtering device 10 of the prior art, and the test tube 32 with which the same is used as described above, are normally simply disposed of after use.

Although the liquid filtering device 10 of the prior art unquestionably functions effectively as described to provide a quantity of essentially "pure" blood serum in the internal space 14 of tubular body member 12, and has accordingly gained and continues to enjoy very wide commercial acceptance to that effect, it will nonetheless be clear to those skilled in this art that careful visual observation through the transparent test tube 32 and the translucent body member 12 are required by the operator to insure that wiper 26 is not inserted into the test tube below the serum layer-buffy layer interface, and to insure that the blood serum reaches the desired level in the body member 12. Thus, the possibility of human error on the part of the operator does become a factor. Too, since the level of the blood sample as a whole, and thus the level of the blood serum layer, in test tube 32 may vary, and especially in instances wherein the test tube 32 is a Vacutainer into which the blood sample is withdrawn directly from a patient and "short" (less than a normal amount of blood sample) or "long" (more than a normal amount of blood sample) pulls occur, it will be clear that the level of the blood serum within internal space 14 of body member 12 may also vary; and this can present difficulties in instances wherein the test tube 32 is subsequently mounted on a carrier block (not shown) for address by automatic aspirating probe means of limited, fixed travel in contemporary automated blood analysis systems. In addition, and unless great care is taken by the operator, a blood sample of extraordinarily large volume in test tube 32 can, of course, result in blood serum spillage through body member top opening 16 and/or vent 24 upon insertion of the prior art liquid filtering device 10 into test tube 32 to too great an extent.

Figure 3:
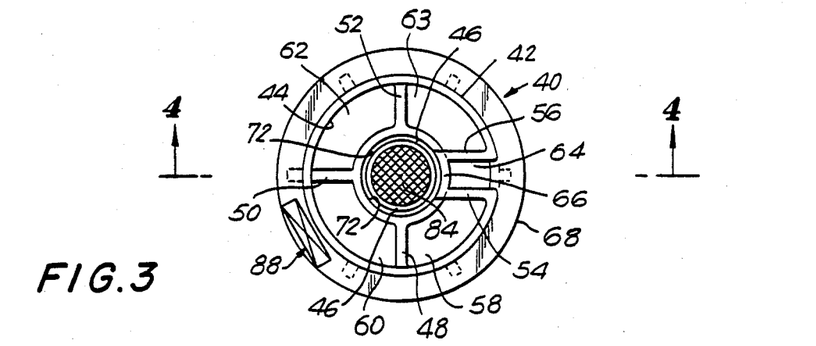
FIG. 3 is a top plan view of a new and improved liquid level adjusting and filtering device representatively configured and operable in accordance with the teachings of our inveniton.
Figure 4:
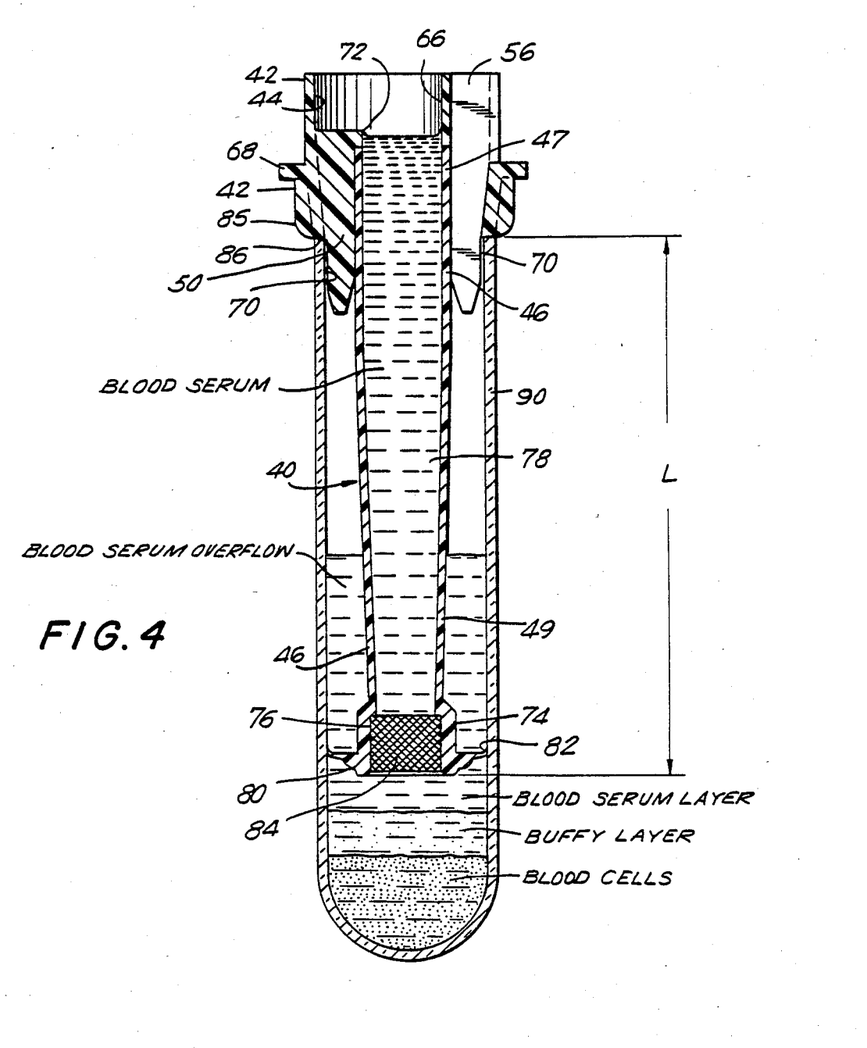
FIG. 4 is a cross sectional view taken essentially along line 4—4 in FIG. 3, and depicts the device of our invention in operable relationship with a liquid container.

Referring now to FIGS. 3 and 4, a new and improved, liquid level adjusting device representatively configured and operable in accordance with the teachings of our invention is indicated generally at 40, and comprises a generally tubular cap member 42 having a generally central opening 44; and an integral, generally frusto-conical tubular body member 46 supported therefrom in said opening in manner generally concentric therewith to extend downwardly therefrom by spaced, generally radially extending support ribs 48, 50 and 52, and by generally parallel, more closely spaced support ribs 54 and 56. This results in the formation of cap member overflow openings 58, 60 62 and 63; and in the formation of a cap member vent opening 64 which is separated from the overflow openings 58 and 63 by ribs 54 and 56, and which is separated form the top opening in the tubular body member 46 by an arcuate cap member dam or wall member 66 joined to ribs 54 and 56 as best seen in FIG. 1.

Further included in the cap member 42 is a generally circular mounting flange 68; and a generally cylindrical skirt 70 formed as shown to essentially surround the lower portion of the cap member, and sized in accordance with the opening in a teat tube or like container to fit snugly therewithin upon use of the device 40 therewith as described in detail hereinbelow.

Tubular body member 46 includes an upper, generally cylindrical portion 47 forming a liquid reservoir which is open, and thus readily accessible, at the upper end 72 thereof; and an integral, lower generally frusto-conical portion 49 forming a transport tube for the supply of liquid to reservoir 47. Body member 46 terminates as shown in an enlarged, generally cylindrical lower end portion 74 which includes a stepped opening 76. Thus, body member 46 will be seen to define an internal space 78 which is in communication with both top opening 72 and bottom opening 76.

A generally torus-like wiper 80 is formed as shown integrally with body member end portion 74 to extend radially outwardly thereof in manner generally concentric with body member opening 76. Wiper 80 includes an outer edge or rim portion 82 of reduced thickness so as to be somewhat flexible; and the outer diameter of this edge or rim portion 82 is slightly greater than the outer diameter of skirt 70.

A generally cylindrical, mesh-like filter is indicated at 84, and is disposed as shown in stepped opening 76 in body member 46, and retained therein in any suitable manner, for example by press fitting.

Further included in cap member 42 is a generally torus-like shoulder 85 which includes an essentially flat bottom surface 86 formed as shown immediately above skirt 70, and which is effective as described in detail hereinbelow to function as a stop to automatically determine or limit the extent to which the liquid level adjusting device 40 of our invention can be inserted into a test tube or like container. An identification label or the like is indicated at 88 in FIG. 1, and is affixed as shown to cap member mounting flange 68 to identify the sample liquid with which the device 40 is to be utilized.

The cap member 42 and integral body member 46 are preferably made from any readily available, inexpensive, suitably translucent and appropriately chemically inert material such as polyethylene, and are preferably fabricated as a unit by well known molding techniques; while filter 84 is preferably made from high density ployethylene mesh of appropriate pore size.

In representative use to automatically adjust the level of and filter the upper or blood serum layer of a blood sample which has been withdrawn from a patient into a Vacutainer as indicated at 90 in FIG. 4 and centrifuged in the same to result in the separation of the blood sample into respective blood cell, buffy and blood serum layers as identified as such in FIG. 4, it may be understood that the device 40 of our invention is carefully but firmly inserted into the open top of the Vacutainer and moved downwardly therein until the flat surface or stop 86 abuts the top edge of the Vacutainer to thus prevent further downward movement of the device, and result in the device 40 being positioned relative to the Vacutainer 90 as depicted in FIG. 4, with skirt 70 functioning to form an esstentially liquid-tight seal with the relevant upper porion of the inner Vacutainer wall. As wiper 80 enters the Vacutainer 90 and progresses downwardly therein, the outer edge or rim portion 82 of the wiper will flex upwardly as shown to a slight extent to form an essentially fluid-tight seal with the inner Vacutainer wall. Accordingly, the wiper will act as a positive displacement pump vis-a-vis the upper or blood serum layer; and will operate to force the same to flow upwardly through filter 84 in opening 76 into internal space 78 of the body member 46; it being clear that the air which is entrapped below the wiper 80 as the same moves downwardly in Vacutainer 90 will ultimately simply bubble up through the blood serum layer for esxape to atmosphere through top opening 72 in the body member 46. Of course, this results in the filtering of unwanted materials in the nature of fibrin or clotted proteins or the like from the thusly pumped blood serum.

In most instances—as supported by field experience and careful testing of Vacutainer pulls to determine consistently representative hematocrit levels, and predetermination in accordance therewith of the length L of FIG. 4 from stop 86 to the bottom of body member 46, and of the volume of internal space 78 vis-a-vis the overall length and volume of Vacutainer 90—the insertion as described of device 40 into Vacutainer 90 to the point where stop 86 abuts the top edge of the Vacutainer to positively limit further downward movement of the device, will result not only in the wiper 80 coming to rest as shown in FIG. 4 well within the blood serum layer but above the blood serum layer-buffy layer interface to thus insure that only blood serum is pumped as described by the wiper 80 into internal space, but will also result in sufficient blood serum being pumped as described by the wiper 80 to completely fill and overflow the internal space 78 in body member 46; with the excess thusly pumped blood serum simply draining back through overflow openings 58, 60, 62 and 63 in cap member 42 to come to rest as depicted in FIG. 4 above the wiper 80 back within Vacutainer 90. This is to say that sufficient blood serum will be pumped as described by wiper 80 through body member transport tube 49 to completely fill and overflow body member reservoir; while blood sample spillage, as is particularly undesirable in a medical diagnostic environment, is prevented. Ambient air within Vacutainer 90 but without internal space 78 will simply be displaced by the return flow of this blood serum overflow for return to atmosphere through cap member vent opening 42. For use, for example, of the device 40 with a 16×75 mm Vacutainer of 10 ml capacity (Becton-Dickinson Part No. 6533) which is designed to pull approximately 7 ml or less of whole blood, a representative length L from stop 86 to the bottom of body member 46 would be 47 mm.

Under the above circumstances, it will be clear to those skilled in this art that the liquid level adjusting device of our invention will, when utilized as described in conjunction with Vacutainer 90, automatically and effectively provide blood serum at a consistently repeatable, and readily accessible, location relative to the Vacutainer at the upper edge of opening 72 in reservoir 47 of body member 46.

For use in contemporary blood sample analysis systems in the nature of that disclosed, for example, in currently pending application of Steve Saros, et al, for U.S. Pat. Ser. No. 441,181 filed Nov. 11, 1982 and assigned to the assignee hereof and now indicated as containing allowable subject matter, wherein a series of blood serum samples are presented in turn to aspirating probe means for successive, automated aspiration of like, predetermined blood serum quantities, and successive automated analyses thereof with regard to a variety of blood serum constituents, it may be understood that a plurality of the liquid level adjusting device—Vacutainer combinations of FIG. 4, each containing a blood serum sample at the same, readily accessible level as described at the upper edge of opening 72 in body member 46, would be disposed through use of mounting flange 68 on a carrier block or like sampler device for presentation in turn to the aspirating probe means.

Figure 5:
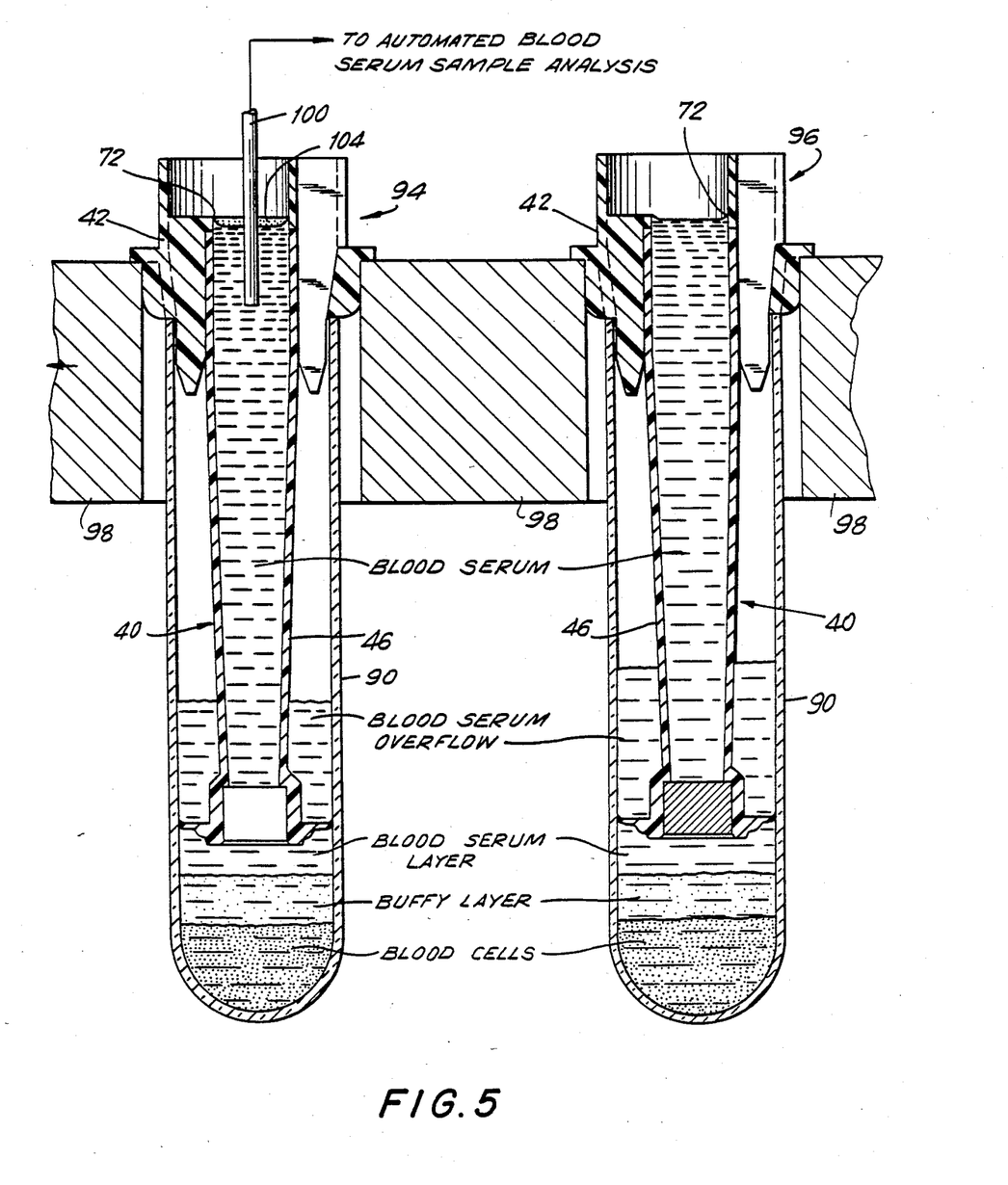
FIG. 5 depicts two of the devices of our invention in cross section as disposed in operatively adjacent positions on a carrier block of a representative automated sample liquid analysis system.

This is clearly illustrated by FIG. 5 wherein two of the liquid level adjusting device—Vacutainer combinations of FIG. 4, as respectively generally indicated at 94 and 96 in FIG. 5, are depicted as disposed in operatively adjacent positions on a carrier block as depicted at 98; and it will be clear that the respective levels of the blood serum samples in each of the devices 40 at the respective upper edges of the opeinings 72 in the device body members 46 are precisely the same vis-a-vis the carrier block 98. Accordingly, and as will be clear to those skilled in this art, these levels will also be precisely the same regarding aspirating probe means as indicated schematically at 100 in FIG. 5 and disposed in operative relationship to liquid level adjusting device—Vacutainer combination 94 for aspiration of a predetermined blood serum sample quantity therefrom. These aspirating probe means may, for example, take the form of those disclosed in U.S. Pat. No. 4,121,466 issued Oct. 24, 1978 to Allen Reickler, et al, and assigned to the assignee hereof.

Another representative automated blood sample analysis system with which the liquid level adjusting device of our invention finds ready utilization is that disclosed in U.S. Pat. No. 4,253,846 issued Mar. 3, 1981 to William J. Smythe, et al, and assigned to the assignee hereof.

Of particular advantage with regard to use as described of the liquid level sdjusting device of our invention in automated blood sample analysis systems of the nature specified by way of representative example is the fact that, with the blood serum sample always presented to the system aspirating probe at the same precisely repeatable level, devices which operate to sense blood serum sample level and control the extent of vertical movement of the aspirating probe accordingly, are rendered totally unnecessary; it being well understood by those skilled in this art that the incorporation and use of such level sensing devices in automated analysis systems of the nature specified which utilize an immiscible isolation liquid, or "oil," to greatly reduce blood serum sample carryover, is most difficult, and adds materially to the cost and complexity of such systems. Too, with the blood sample serum always at the same precisley repeatable level vis-a-vis the aspirating probe for each of the blood samples of interest, it will be clear that vertical aspirating probe travel may be substantially shortened—as in any event required by a fixed probe service loop length in the system of copending application for U.S. Pat. Ser. No. 441,181—the thus contributing materially to increased speed of overall analysis system operation as will be obvious.

If desired, the filter 84 may have impregnated or otherwise contained therein an appropriate chemical material for pre-analysis treatment of the blood serum as the same is pumped therethrough as described. This chemical material may take the form of an appropriate surfactant to lower the surface tension of the blood serum and inhibit pre-analysis settling of relevant serum components; or may take the form of an appropriate preservative to inhibit pre-analysis serum deterioration and/or oxidation. Of course, other and different chemical materials would come within the purview of this concept.

Figure 6:
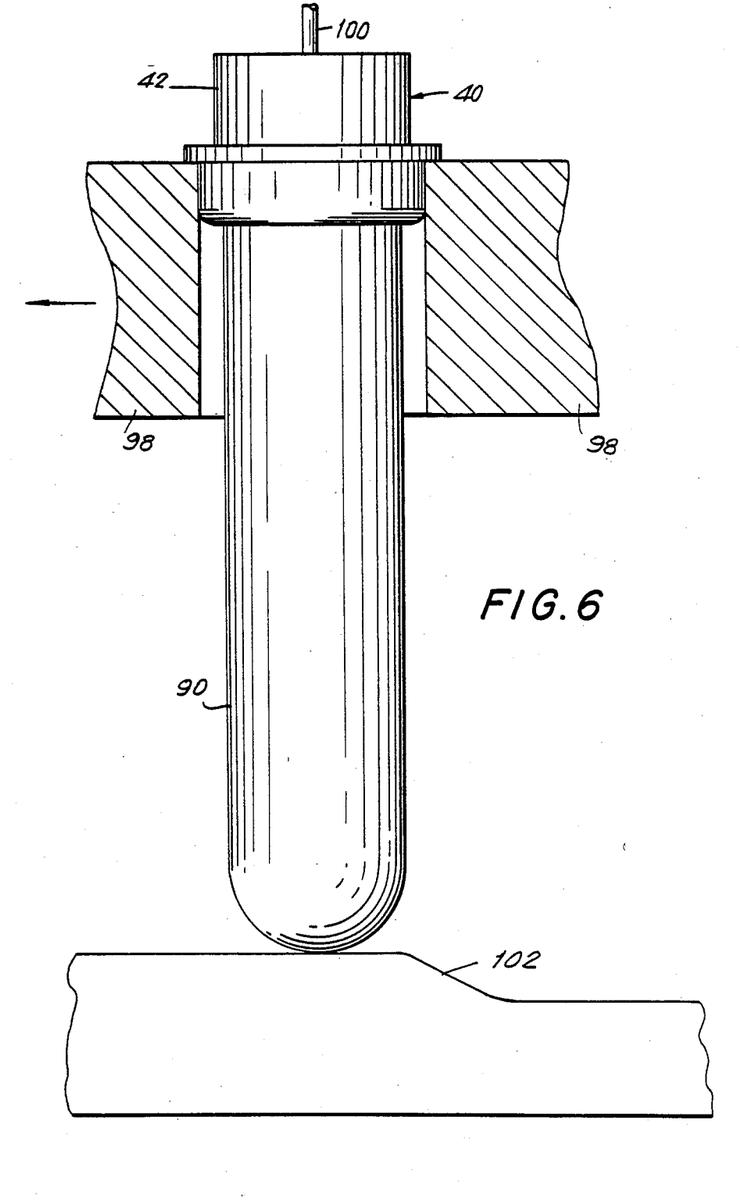
FIG. 6 is a somewhat diagrammatic side view depicting means in accordance with the teachings of our invention for compensating for pre-analysis sample liquid evaporation.

For use in instances wherein relatively long blood serum residence times in the device 40 on the carrier block 98 are anticipated, to thus give rise to the possibility of clinically significant serum evaporation, e.g. evaporation sufficient to reduce the level of the blood serum below the upper edge of opening 72 to a not immaterial extent, the operator may be instructed to incompletely insert the device 40 into the Vacutainer 90, leaving some measure of space between stop 86 and the upper edge of Vacutainer 90, and means provided in the sample analysis system to automatically complete device insertion into the Vacutainer just prior to presentation thereof to the aspirating probe, thus insuring blood serum at the desired level attendant such presentation. These means may, for example, take the form of the inclined plane as indicated at 102 in FIG. 6 and which is disposed as shown in the path of travel of the bottoms of the Vacutainers 90 as the same are moved along with the incompletely inserted liquid level adjusting devices 40. Accordingly, and with carrier block movement in the direction indicated by the arrow in FIG. 6, it will be clear to those skilled in this art that as the bottom of each Vacutainer 90 in brought into contact in turn with the inclined plane 102, the Vacutainer will be forced upwardly to bring the upper Vacutainer edge into firm contact with device stop 86; thus completing device insertion by upward movement of the Vacutainer relative thereto, and insuring the replenishment by the pumping action as described of the device wiper 80 of the blood serum in internal space 78 to the desired level of the edge of opening 72. Of course, operation as described of the inclined plane 102 will require that the cap member 42 of the liquid level adjusting device 40 of our invention be gripped firmly in the carrier block 98 to prevent upward movement thereof in response to upward movement as described of the Vacutainer 90 in each instance.

For use in contemporary, automated blood sample analysis systems of the nature discussed hereinabove wherein an isolation liquid or "oil," which is immiscible with the blood serum samples of interest, is utilized in conjunction with the system aspirating probe means to minimize blood serum sample carryover, i.e. the contamination of a succeeding blood serum sample by the residue of a preceding blood serum sample, and wherein a small quantity of said isolation liquid is disposed atop each serum sample pior to serum sample aspiration by the aspirating probe means, it has been determined to be essential to satisfactory analysis system operation that the meniscus of the serum sample at opening 72 at the top of reservoir 47 be "negative" or concave to suitably retain this isolation liquid quantity thereon. Since, with sample liquids constituted as representatively described by blood sera, and with the liquid level adjusting device 40 of our invention representatively constituted as described by polyethylene which is normally hydrophobic, this meniscus would normally be "positive" or convex and thus incapable of retaining the isolation liquid quantity of interest atop the aqueous blood serum sample, it has been determined in further accordance with the teachings of our invention that the polyethylene must be appropriately formulated, or treated, to render the same hydrophilic thus providing for the requisite "negative" or concave meniscus, and attendant isolatliquid quantity retention atop the blood serum samples of interest. This polyethylene formulation may, for example, take the form of the addition of an appropriate surfactant or the like to the same to render the material hydrophilic; while this polyehtylene treatment may, for example, take the form of the appropriate etching or the like of the device 40, or at least of the relevant portion thereof at the upper edge of reservoir 47, prior to use of the device in analysis systems of the nature under discussion.

With the polyethylene appropriately formulated or treated as representatively described to render the same hydrophilic, it will be clear to those skilled in this art that the meniscus of the blood serum samples of interest at the upper edge of reservoir 47 will be "negative" or concave as shown in FIGS. 4 and 5 of the drawings; whereby the immiscible isolation liquid quantity as representatively indicated at 104 in FIG. 5 for the "leading" blood serum sample of interest will be suitably retained atop the latter.

Although the size of the liquid level adjusting device 40 of our invention will vary in accordance with the abovedescribed parameters with regard to the size of the Vacutainer 90, it is preferable that the wall thicknesses of the tubular body member 46, and the volume of internal space 78, be made as small as practicable to displace the minimum amount of blood serum compatible with the satisfactory function of the device, and effectively accomodate the widest possible range of variations in Vacutainer pulls.

Since, as made clear hereinabove, the liquid level adjusting and filtering funtions of the device 40 are essentially independent, it will be clear to those skilled in this art that the device can be made without the filter 84 for operational use solely for automatic liquid level adjusting purposes as described.

Although disclosed by way of representative example as applied to blood samples which are collected and centrifuged for separation in Vacutainers, it will be clear that the device 40 of our invention is by no means limited to such use, but rather, would be equally suitable for use with a wide range of other and different liquids, which need not necessarily be layered, as contained in a wide range of other and different containers. Too, there is, of course, no requirement that the liquids in question be for analysis.

Of course, the sample liquid level adjusting and filtering device 40 of our invention, and the Vacutainer 90 with which the same is used as representatively described, are simply discarded after use; it being clear to those skilled in this art that the choice of inexpensive materials and method of fabrication for the device 40 assures the realistic production thereof in large quantities at vey low device unit cost.

Various changes may be made in the hereindisclosed preferred embodiments of our invention without departing from the spirit and scope as defined in the appended claims.

What is claimed is:

1. In a liquid level adjusting device for use in each instance with one of a plurality of like, open-topped generally vertically oriented containers which respectively contain liquids therein at different levels to adjust those liquid levels to substantially the same predetermined liquid level location relative to each of the containers, the improvements comprising, said device including, liquid reservoir means supportable from the container and accessible from without the container to permit the removal of liquid from said liquid reservoir means, said liquid reservoir means comprising means for fixing the location of said reservoir means at substantially the same location relative to the container in each instance, liquid transport means operatively connected to said liquid reservoir means and insertable into said container for supplying liquid from said container to said reservoir means for substantially filling said reservoir means with liquid upon insertion of said liquid transport means into said container sufficient to enable the level of said liquid in said container to be adjusted in each instance to the location of said substantially liquid-filled reservoir means upon the insertion of said liquid transport means into the container.

2. In a liquid level adjusting device as in claim 1 wherein, said location fixing means comprise stop means which are further operable to limit the extent to which said liquid transport means may be inserted into said container.

3. In a liquid level adjusting device as in claim 2 wherein, said liquid in said container comprises a plurality of vertically arranged layers of liquids of different characteristics, and wherein said liquid transport means are dimensioned relative to said container so that insertion of said liquid transport means into the liquid in said container to the extent permitted by said stop means will limit the insertion of said liquid transport means into the uppermost of said liquid layers, only.

4. In a liquid level adjusting device as in claim 1 comprising, filter means operatively associated with said liquid transport means and operable to filter said liquid attendant the supply thereof to said reservoir means.

5. In a liquid level adjusting device as in claim 4 further comprising, liquid treatment means operatively associated with said filter means for treating said liquid attendant the supply thereof to said reservoir means.

6. In a liquid level adjusting device as in claim 1 wherein, said reservoir means are hydrophilic.

7. In a liquid level adjusting device as in claim 1 wherein, said reservoir means comprise a generally open-topped cylindrical member supportable at the upper portion of said container, and said liquid transport means comprise a generally tubular member extending downwardly from said reservoir means into said container and in liquid-flow communication with said reservoir means.

8. In a liquid level adjusting device as in claim 7 wherein, said generally tubular liquid transport means member is frusto-conical.

9. In a liquid level adjusting device as in claim 1 wherein, said reservoir means comprise overflow means for flowing liquid therefrom upon the substantial filling thereof with liquid by said liquid transport means.

10. In a liquid level adjusting device as in claim 9 wherein, said liquid reservoir means overflow means are in liquid-flow communication with said container whereby, liquid overflowing from said reservoir means will flow therefrom through said overflow means for return to said container.

11. In a liquid level adjusting device as in claim 1 wherein, said liquid reservoir means are operable to substantially seal said container, and said liquid reservoir means comprise vent means for venting said container to atmosphere whereby, ambient air displaced from said container upon the insertion of said liquid transport means thereinto will be vented to atmosphere through said reservoir means vent means.

12. In a sample analysis system which is operable to successively analyze in turn a series of sample liquids as supplied thereto in separate, like containers, said sample liquids intially being at different levels in said containers, said system including aspirating probe means for successively aspirating in turn like quantities of said liquids from said containers for analysis by said sample liquid analysis system, and means to present said containers in turn to said aspirating probe means at substantially the same container location, the improvements comprising, liquid level adjusting means operatively connected to each of said containers for adjusting the respective levels of the sample liquids contained therein to substantially the same sample liquid level location relative to each of the containers sufficient to enable said sample liquids to be presented in turn in said containers to said aspirating probe means at substantially the same liquid level location relative to said aspirating probe means.

13. In a sample analysis system as in claim 12 wherein, each of said containers is open-topped and generally vertically oriented by said means which present said containers in turn to said aspirating probe means, and wherein said liquid level adjusting means comprise, liquid reservoir means supportable from each of the containers and accessible from without the container to permit the removal of liquid from the liquid reservoir means by said aspirating probe means, said liquid reservoir means comprising means for fixing the location of said reservoir means at substantially the same location relative to the container in each instance, liquid transport means operatively connected to said liquid reservoir means and insertable into the liquid in the container for supplying said liquid to said reservoir means for substantially filling said reservoir means with liquid upon insertion of said liquid transport means into the container, whereby the level of the liquid in the container will be adjusted in each instance to the location of said substantially liquid-filled reservoir means upon the insertion of said liquid transport means into the container.

14. In a sample liquid analysis system as in claim 13 wherein, said reservoir means are hydrophilic.

15. In a sample liquid analysis system as in claim 13 wherein, said location fixing means comprise stop means which are further operable to limit the extent to which said liquid transport means may be inserted into said container.

16. In a sample analysis system as in claim 15 further comprising, means operatively associated with said containers, said container presentation means, and said liquid level adjusting means for inserting said liquid transport means into said containers to the extent permitted by said stop means prior to the presentation of the containers in turn to said aspirating probe means.

17. In a sample analysis system as in claim 15 wherein, the sample liquids in each of said containers comprise a plurality of vertically arranged layers of liquids of different characteristics, and wherein said liquid transport means are dimensioned relative to said containers so that insertion of said liquid transport means into the liquid in said containers to the extent permitted by said stop means will in each instance limit the insertion of said liquid transport means into the uppermost of said liquid layers, only.

* * * * *